US006395018B1

(12) United States Patent
Castaneda

(10) Patent No.: US 6,395,018 B1
(45) Date of Patent: May 28, 2002

(54) ENDOVASCULAR GRAFT AND PROCESS FOR BRIDGING A DEFECT IN A MAIN VESSEL NEAR ONE OF MORE BRANCH VESSELS

(76) Inventor: Wilfrido R. Castaneda, 2 Stilt St., New Orleans, LA (US) 70124

( * ) Notice: Subject to any disclaimer, the term of this patent is extended or adjusted under 35 U.S.C. 154(b) by 0 days.

(21) Appl. No.: 09/020,869

(22) Filed: Feb. 9, 1998

(51) Int. Cl.[7] ................................................. A61F 2/00
(52) U.S. Cl. ..................... 623/1.13; 623/1.35
(58) Field of Search ............................. 623/1.11, 1.13, 623/1.16, 1.19, 1.21, 1.23, 1.34, 1.35

(56) References Cited

U.S. PATENT DOCUMENTS

| | | | |
|---|---|---|---|
| 3,657,744 A | | 4/1972 | Ersek |
| 4,512,338 A | | 4/1985 | Balko et al. |
| 4,562,596 A | | 1/1986 | Kornberg |
| 5,399,352 A | * | 3/1995 | Hanson .......................... 623/1 |
| 5,425,765 A | * | 6/1995 | Tiefenbrun ..................... 623/1 |
| 5,464,450 A | * | 11/1995 | Buscemi .......................... 623/1 |
| 5,522,961 A | | 6/1996 | Leonhardt |
| 5,591,195 A | | 1/1997 | Taheri et al. |
| 5,609,628 A | * | 3/1997 | Keranen ......................... 623/1 |
| 5,617,878 A | | 4/1997 | Taheri |
| 5,653,743 A | * | 8/1997 | Martin ........................... 623/1 |
| 5,676,697 A | * | 10/1997 | McDonald ..................... 623/1 |
| 5,683,453 A | * | 11/1997 | Palmaz .......................... 623/1 |
| 5,824,040 A | * | 10/1998 | Cox ................................ 623/1 |
| 5,855,600 A | * | 1/1999 | Alt ................................ 623/1 |

FOREIGN PATENT DOCUMENTS

| | | |
|---|---|---|
| EP | 0 646 365 A | 4/1995 |
| WO | WO 95 01761 A | 1/1995 |
| WO | WO 97 09008 A | 3/1997 |
| WO | WO 97 25001 | 7/1997 |

OTHER PUBLICATIONS

World Medical News, vol. 5, Issue 6, May 1997.
Evert–Jan Verschuyl, et al., "Renal Artery Origins: Location and Diameter in the Transverse Plane at CT", Radiology, vol. 203, pp. 71–75, Apr. 1997.
Hodgson et al., "Shape Memory Alloys", ©1995.
Brice, "New Devices Enliven Interventional Practice", Diagnostic Imaging, Mar. 1997.
Taheri, et al., "The Talent™ Endoluminal Graft Placement System", p. 433–445.
"Talent™ Endolunminal Stent Graft System", World Medical Manufacturing Corporation, ©1997.

* cited by examiner

Primary Examiner—Michael J. Milano

(57) ABSTRACT

An endovascular graft for bridging a defect in a main vessel near one or more branch vessels is provided. A graft, consistent with one embodiment of the invention, includes a tubular member which defines one or more apertures and is adapted for expansion against inner wall of a main vessel above one or more branch vessels. Each aperture defined by the tubular member is alignable with at least one of the one or more branch vessels and may have an area which is as large as or larger than the opening of the respective branch vessel(s) when the tubular member is expanded against the inner wall of the main vessel. Embodiments of the invention are particularly suited for bridging abdominal aortic aneurysms having short or no proximal necks, a significant factor limiting the use of conventional grafts for bridging abdominal aortic aneurysms.

23 Claims, 12 Drawing Sheets

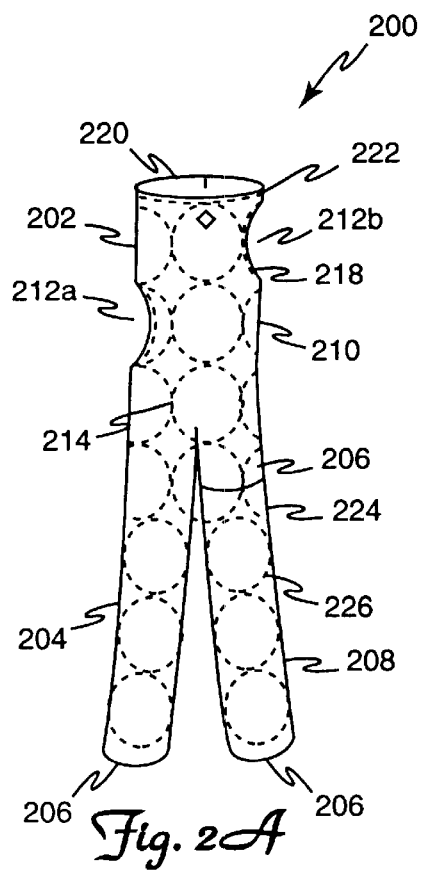 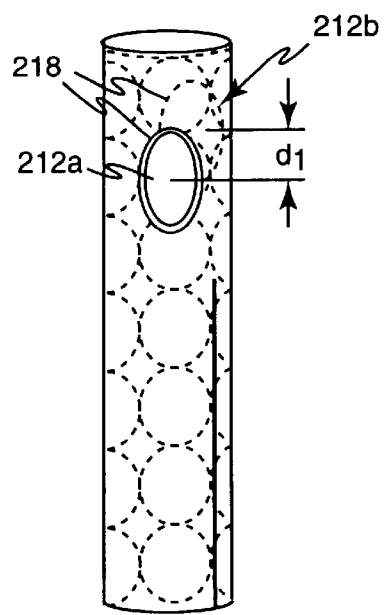
Fig. 2A  Fig. 2B
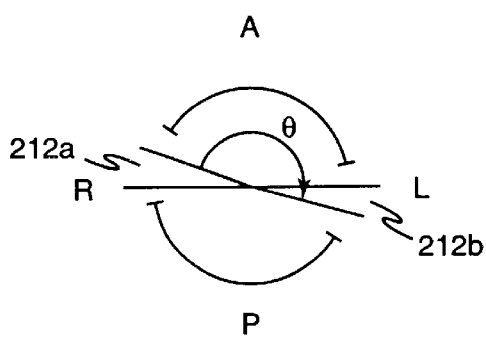
Fig. 2C

ENDOVASCULAR GRAFT AND PROCESS FOR BRIDGING A DEFECT IN A MAIN VESSEL NEAR ONE OF MORE BRANCH VESSELS

FIELD OF THE INVENTION

The present invention generally relates to endovascular grafts and, more particularly, to a graft and process for bridging an abdominal aortic aneurysm disposed in the aorta near the renal arteries in which the graft is expanded against a portion of the aortic wall above one or both renal arteries.

BACKGROUND OF THE INVENTION

Abdominal aortic aneurysms are potentially life threatening defects which generally lie in a section of the aorta between the renal arteries and the iliac arteries. In some cases, an abdominal aortic aneurysm may extend into either or both of the iliac arteries.

Abdominal aortic aneurysms are commonly treated using surgical techniques. Surgical treatment of abdominal aortic aneurysms is however a complicated procedure associated with high risk. As an alternative to surgery, a wide variety of grafts including, for example, stented grafts or stent-grafts, have been proposed for bridging and excluding abdominal aortic aneurysms. The use of these grafts is however limited. In most cases, an abdominal aortic aneurysm is either left untreated or is treated surgically. Even in cases using a graft, the procedure is sometimes terminated in favor of surgical treatment.

SUMMARY OF THE INVENTION

The present invention generally provides grafts for bridging a main vessel having a defect disposed near one or more branch vessels extending from the main vessel. Embodiments of the invention are particularly suited for bridging abdominal aortic aneurysms having minimal or no proximal necks, a significant factor limiting the use of conventional grafts for bridging abdominal aortic aneurysms.

One particular embodiment of the invention provides a stent-graft for bridging an aneurysm in an aorta disposed below two renal arteries. The stent-graft includes a graft material defining two renal apertures each oriented to align with one of the two renal arteries when the stent-graft is in an expanded state. The stent-graft further includes a stent system for supporting the graft material in a contracted state wherein the renal apertures are contracted and the expanded state wherein the renal apertures are expanded. The stent system when in the expanded state, is adapted to press against a portion of the aortic wall above the first renal artery and against a portion of the aortic wall above the second renal artery. Each renal aperture may, for example, have an area as large as or larger than the opening of the respective renal artery.

In accordance with another embodiment of the invention, the graft material defines a mesenteric aperture oriented to align with a superior mesenteric artery when the stent-graft is in an expanded state. In accordance with yet another embodiment of the invention, the stent-graft material further defines a celiac aperture oriented to align with a celiac axis artery when the stent-graft is in the expanded state.

A graft, consistent with another embodiment of the invention, includes a tubular member which defines one or more apertures and is adapted for positioning against a wall of a main vessel above one or more branch vessels. Each aperture defined by the tubular member is alignable with at least one of the one or more branch vessels and has an area which is greater than the opening of the respective branch vessel(s) when the graft is positioned against the wall of the main vessel.

In accordance with another aspect of the invention, a process of bridging a defect disposed in a main vessel near one or more branch vessels is provided. Consistent with the process, a graft which defines one or more apertures is inserted in a contracted state within the main vessel. The graft is aligned within the main vessel such that each aperture aligns with at least a respective one of the branch vessels and expanded into a expanded state wherein the one or more apertures align with the one or more branch vessel and the graft presses against the main vessel wall. The process can, for example, be used to bridge an abdominal aortic aneurysm disposed in an aorta near the renal arteries.

In accordance with another aspect of the invention, a process for manufacturing a customized graft for bridging a defect disposed in a main vessel near one or more branch vessels is provided. The process includes developing a three dimensional image of an interior of the main vessel including the one or more branch vessels. Using the three dimensional image, a customized graft is formed having one or more apertures configured to align with the one or more branch vessels when the graft is positioned against the wall of the main vessel.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIGS. 2A–2C illustrate an exemplary graft in accordance with one embodiment of the invention;

Figure 1:
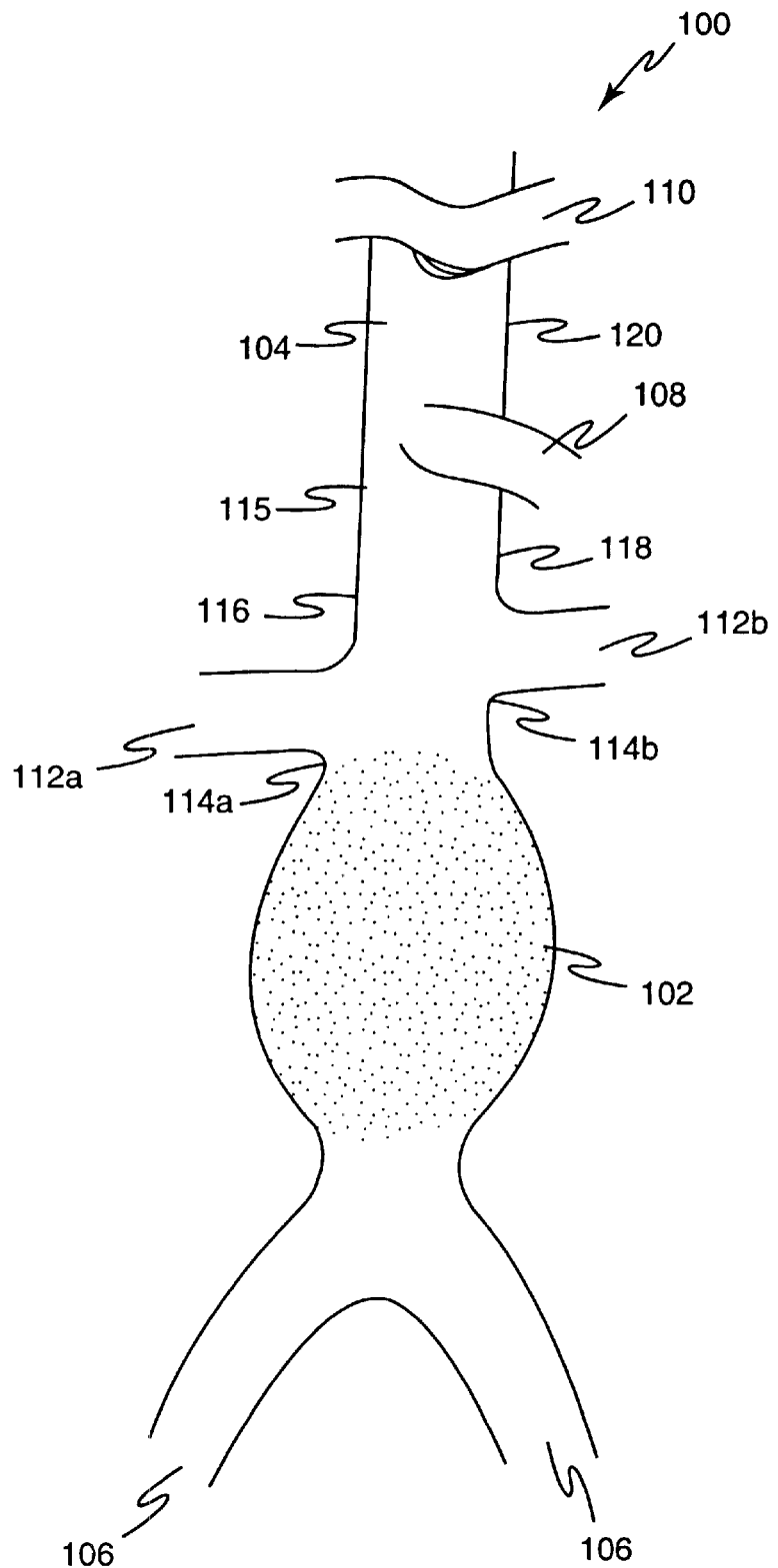
FIG. 1 illustrates a vascular section having an abdominal aortic aneurysm.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

The present invention generally relates to endovascular grafts used for bridging a defect in a main vessel near one or more branch vessels. The invention is particularly suited for bridging and excluding abdominal aortic aneurysms located near the renal arteries. While the present invention is not so limited, an appreciation of various aspects of the invention will be gained through a discussion of the examples provided below.

The invention provides a graft for bridging a defect disposed in a main vessel near one or more branch vessels. The graft includes a tubular member which defines one or more apertures and is adapted for expansion against a portion of the main vessel wall above one or more branch vessels (i.e., against a portion of the main vessel wall opposite the defect). Each aperture defined by the end portion is alignable with at least one of the one or more branch vessels and typically has an area which is as large as or larger than the orifice of the respective branch vessel(s) when the tubular member is expanded against the inner wall of the main vessel. By way of example, in the discussion below, emphasis will be placed on grafts for bridging abdominal aortic aneurysms. However, the invention is not so limited. Other types of defects (e.g., pseudo-aneurysms and post-traumatic fistulas) which are located at the intersection of other body vessels (e.g., iliac bifurcation) are intended to be covered by the invention. Moreover, while the exemplary embodiments below illustrate the use of stented grafts, the invention is not limited thereto.

FIG. 1 illustrates a front view of a exemplary vascular section 100 having a typical abdominal aortic aneurysm 102. The vascular section 100 includes an aorta 104 which bifurcates into two iliac arteries 106, a superior mesenteric artery 108, a celiac axis artery 110, and right and left renal arteries 112a and 112b, each of which branch off from the aorta 104. The renal arteries 112a and 112b may lie at the same or different levels and may be single or multiple in number. In the illustrated vascular section 100, the right renal artery 112a is shown below the left renal artery 112b. A more detailed discussion of the location of renal artery origins can be found in Verschuyl et al., "Renal Artery Origins: Location and Distribution in the Transverse Plane at CT," Radiology 1997, Vol. 203, pp. 71–75, April 1997.

The abdominal aortic aneurysm 102 generally lies in a section of the aorta 104 below the right and left renal arteries 112a and 112b and above the iliac arteries 106. In some cases, the aneurysm 102 may extend into either or both of the iliac arteries 106. As is typical of many abdominal aortic aneurysms, the illustrated aneurysm 102 has no proximal neck (e.g., the aneurysm extends up to and abuts the lower edges 114a and 114b of the right and/or left renal arteries 112a and 112b).

Conventional grafts used to bridge abdominal aortic aneurysms typically have a proximal end designed for positioning against a proximal neck, i.e., a patent portion of the aortic wall below the renal arteries 112a and 112b. Typically, necks greater than 10 millimeters (mm) are needed to reliably secure a conventional graft. With, necks less than 5 mm conventional grafts typically cannot be reliably secured. One conventional graft which attempts to address the problems associated with minimal proximal necks includes a webbed end which may be positioned slightly over the lower edge 114a of the right renal artery 112a. This graft however still requires some neck in order to adequately seal the proximal end of the graft and sufficiently retain the graft within the aorta. Moreover, the webbed end can partially obstruct flow through the lower renal artery 112a. The present invention overcomes the limitations of conventional grafts and provides an endovascular graft and process for bridging abdominal aortic aneurysms having minimal (e.g., less than 5 or 10 mm) or no proximal necks.

FIGS. 2A–2C illustrate an exemplary stent-graft for bridging an abdominal aortic aneurysm in accordance with an embodiment of the invention. By way of example and not of limitation, reference will be made to the exemplary vascular section 100 discussed above to facilitate understanding of the stent-graft 200. As shown in FIG. 2A, the stent-graft 200 includes a main body 202 which bifurcates into a leg 204 and a stem 206, the latter of which is used to attach a mating leg 208 to the main body 202. The main body 202 of the stent-graft 200 is advantageously adapted for suprarenal fixation. In particular, the main body 202 is configured to expand against portions 116 and 118 of the aortic wall 115 above the renal arteries 112a and 112b. The term above is used herein to describe a vessel wall portion on a side of a branch vessel opposite the side of the branch vessel where a defect lies.

The main body 202 of the stent-graft 200 includes a graft material 210 and a stent system 214 (shown in dashed lines) which supports the graft material 210. The stent system 214 typically has an expanded state for securing the main body 202 within the aorta 104 and is deformable into a contracted state for insertion through the vascular system of a patient. In its expanded state, the stent system 214 typically exerts sufficient force against the aortic wall to retain the main body 202 in place and form a blood-tight seal between the main body 202 and the aortic wall. The main body 202 is shown with the stent system 214 in the expanded state. In its contracted state, the stent system 214 (and main body 202) may take a variety of different forms. In its expanded state, the main body 202 is configured to expand against portions 116 and 118 of the aortic wall 115 above the renal arteries 112a and 112b.

The graft material 210 is typically distensible such that the graft material 210 can adapt to the stent system 214 when the main body 202 is contracted and expanded. The graft material 210 may be formed from a number of different well-known materials, such as Dacron™, Gortex™, polyethylene or polyurethane, for example. The graft material 210 may be secured to the stent system 214 using, for example, well-known stitching, gluing or weaving techniques. While the invention is not so limited, the stent system may be disposed on the exterior or interior of the graft material 210, or within the graft material 210 itself.

The graft material 210 generally defines two renal apertures 212a and 212b each of which are alignable with a respective one of the renal arteries 112a and 112b when the main body 202 is expanded against the aortic wall. The shapes, sizes and relative orientation of the renal apertures 212a and 212b can vary as will be discussed below. The renal apertures 212a and 212b are each typically supported by a surrounding portion 218 of the stent system 214. The surrounding portions 218 of the stent system 214 may be shaped similar to and completely surround the perimeters of the renal apertures 212a and 212b. The renal apertures 212a and 212b may be supported by the surrounding portions 218 of the stent system 214 by, for example, stitching portions of the graft material 210 around the apertures 212a and 212b to the surrounding stent portions. By supporting the perimeter of each aperture with the stent system 214, a tight seal can be formed between the graft material 210 and the aortic wall 115 around the renal artery orifices and leakage can be prevented. While the invention is not so limited, the exemplary stent system 214 is formed of a wire (e.g., nitinol) mesh in a honeycomb pattern having a number of interconnected wire loops, two of the which form surrounding portions 218 and align with the renal apertures 212a and 212b in the graft material 210. The proximal end 220 of the stent system 214 generally seals the main body 202 against the aortic wall 115, and may, for example, include a wire portion 222 interconnecting loops of stent system 214.

The stent system 214 may be formed of a number of different materials including, for example, metals and/or metal alloys. In one embodiment, the stent system 214 is formed from a shape-memory alloy (SMA), such as nitinol. Shape-memory alloys have the ability to transform from a martensite phase shape (in which the stent system 214 may be deformed to a contracted state) to a parent or austenite phase (typically corresponding to the expanded state of the stent system 214). An SMA may exhibit either one-way or two-way shape memory. With two-way shape memory, the SMA changes shape upon both heating and cooling. With one-way shape memory, the SMA undergoes shape change only upon heating. Upon cooling, the shape of the SMA does not spontaneously change, but may be changed by force.

Figure 9:
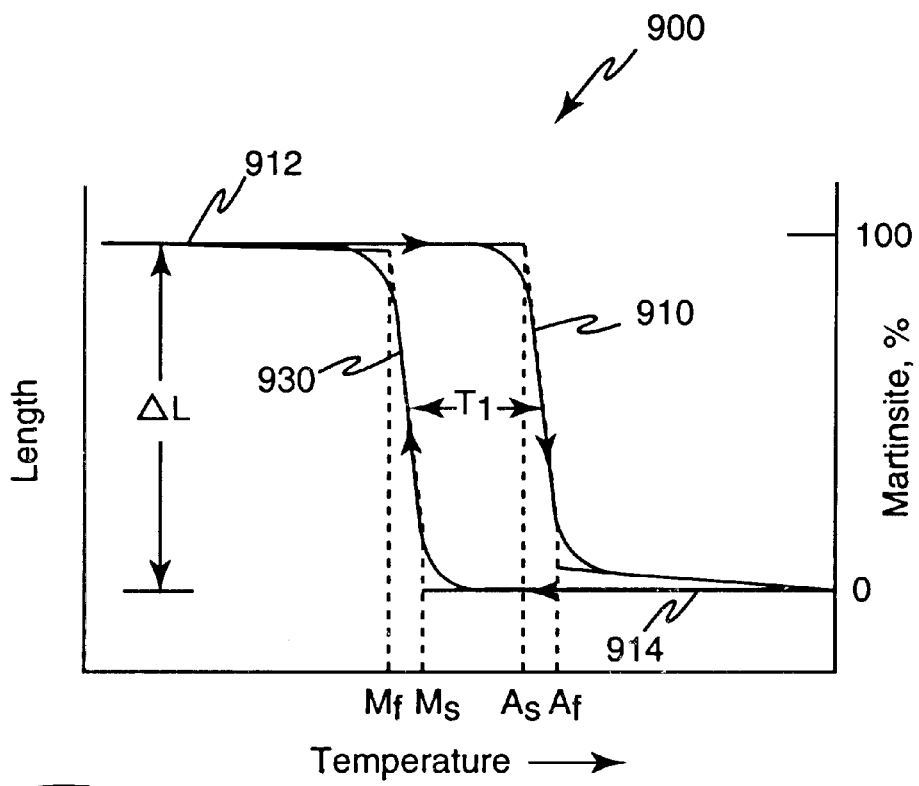
FIG. 9 illustrates a typical temperature vs. transformation curve for a shape memory alloy.

Turning to FIG. 9, there is illustrated a typical transformation vs. temperature curve for an SMA specimen. The curve 900 typically includes a heating curve 910, on which the SMA specimen generally undergoes transformation from a martensite phase 912 to an austenite phase 914, and a cooling curve 930 on which the phase change is reversed. While the phase transformations take place over a relatively broad temperature range, the majority of phase transformation typically occurs over a relatively narrow temperature band. The austenite start and finish (AS and AF) temperatures generally denote temperatures between which the majority of the martensite-to-austenite transformation on the heating curve 910 occurs. The martensite start and finish (MS and MF) temperature denote similar temperatures on the cooling curve 930. As can be seen, the transformation curve 900 exhibits hysteris $T_1$ (i.e., an offset between the heating and cooling curves 910 and 930).

In one particular embodiment of the invention, the stent system 214 is formed from an SMA, such as nitinol, having a AF temperature of about body temperature or less (typically 37° C. or less). This enables the stent system 214 to transform into its parent or austenite phase (typically corresponding to the expanded state of the stent system 214) when subject to body temperature. In another embodiment, the stent system 214 is formed from an SMA, such as nitinol, having an AF temperature greater than body temperature (e.g., an AF temperature of about 48° C.). This enables the stent system 214 to be partially expanded to an intermediate state when between an AS temperature (e.g., 35° C.) and the AF temperature and also allows the stent system 214 to be fully expanded when heated above the AF temperature. In the latter embodiment, the MS temperature of the stent system 214 is typically selected to be below body temperature (e.g., about 20° C.) to prevent partial matertensite transformation when the stent system 214 returns to body temperature. In either embodiment, the stent system 214 may demonstrate one-way or two-way shape change.

Referring back to FIGS. 2A–2C, details of the renal apertures 212a and 212b will be discussed. As noted above, the renal apertures 212a and 212b are located on the main body 202 such that, when expanded, the renal apertures 212a and 212b align with the renal artery orifices of a patient. The size of each renal aperture 212a and 212b is typically selected to be at least as large as the orifice of its respective renal artery 112a and 112b. The size of each renal aperture 212a and 212b can vary as the sizes of renal arteries can vary from patient to patient. Suitable sizes of the renal apertures 212a and 212b range from about 0.8 to 1.0 cm or more in diameter for many applications. The use of renal apertures 212a and 212b which are larger than the renal artery orifices allows for variable position of the renal arteries from patient to patient and by allowing some tolerance in the deployment of the main body 202 of the stent-graft 200.

The shape of the apertures 212a and 212b can also vary and may, for example, be rectangular, circular, or ovular. In the example embodiment, each aperture 212a and 212b is ovular in shape and has a length in the longitudinal direction which is greater than a circumferential width. For example, the length may be about 1.2 to 1.5 cm and the width about 1.0 to 1.2 cm. In other embodiments, each aperture 212a and 212b may have a length in the longitudinal direction which is less than a circumferential width. Moreover, the two renal apertures 212a and 212b may have different shapes and/or sizes. For example, one may be oval-shaped and extended in the longitudinal direction, while the other may be oval-shaped and extended in the circumferential direction. As should be appreciated, stent system 214 can be designed to accommodate various shapes of the apertures 212a and 212b.

The relative orientation of the renal apertures 212a and 212b can vary as well. To illustrate exemplary orientations, the angle θ (shown in FIG. 2C) will be used to define the angular distance between the centers of the apertures 212a and 212b and the distance $d_1$ (shown in FIG. 2B) will be used to define the distance between the centers of the apertures 212a and 212b along the longitudinal axis of the stent-graft 200. Relative orientations having an angle θ ranging between about 72 to 225 degrees, and more typically between about 140 and 185 degrees, and a distance $d_1$ ranging from about 0 to 2 cm would be suitable for many applications.

Highly radiopaque markers may be placed on the main body 202 to facilitate identification of the main body 202 within the aorta 103. Advantageously, radiopaque markers may be positioned near or around each renal aperture 212a and 212b to improve visualization and facilitate alignment of the apertures 212a and 212b. This may be done by, for example, soldering radiopaque material (e.g., gold or platinum) to the portions 218 of the stent system 214 surrounding the apertures 212a and 212b. In addition, a radiopaque aligning system may also be placed on the stent-graft portion 210 to aid in aligning the main body 202 with a desired plane, such as the anterior-posterior or A-P plane. For example, a radiopaque diamond (◊) may be placed on one side of the main body 202 and a radiopaque vertical line (|) on the opposite side such that when the diamond (◊) aligns with the line (|), the stent-graft portion 210 is aligned with the desired plane. A diamond (◊)—vertical line (|) aligning system is illustrated in FIG. 2A. A number of other arrangements, such a pair of parallel lines (||) and a perpendicular line (-) or an X and an O, may be used as well.

As noted above, the main body 202 bifurcates into a leg 204 and a stem 206 which is used to attach a mating leg 208 to the main body 202. While not shown to scale, the pair of legs 204 and 208 are typically designed to extend into the iliac arteries 106 and form a bifurcated distal portion which is often desirable for use with abdominal aortic aneurysms which extend into one or both of the iliac arteries 106. Both the leg 204 and stem 206 may be defined by the stent system 214 and graft material 210. The invention is however not so limited. The leg 204 may, for example, include a separate stent system, such as a simple metal spring interconnected to the stent system 214 by connecting bars, if desired.

The mating leg 208 typically includes a graft material 224 supported by a stent system 226. Similar to the main body 202, the leg 208 includes an expanded state (as shown) and may be deformed into a contracted state. The stent system 226 and graft material 224 may, for example, be similar to that of the main body discussed above (e.g., a graft material supported by a honeycomb-shaped wire mesh). Alternatively, the form and/or material of the stent system 226 and graft material 224 can differ from that of the main body 202. For example, the stent system 226 may be made from a different material including, for example, nitinol which may be contracted to a contracted state and which springs to an expanded state without undergoing a phase change. The stem 206 and mating leg 208 may be configured such that the leg 208 is advanced into the stem 206 and expanded within the stem 206 to retain the leg 208 in place. To facilitate retention within the stem 206, the proximal end of the leg 208 may be flared.

Figure 3A:
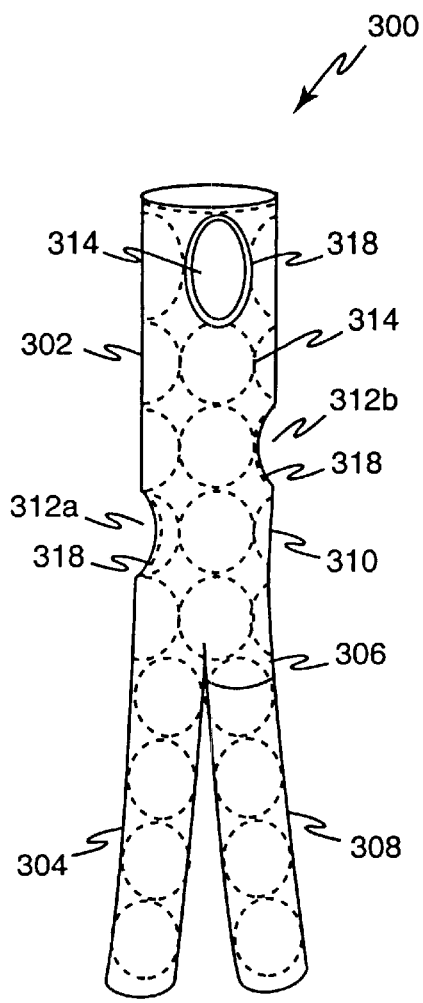
FIGS. 3A–3C illustrate an exemplary graft in accordance with another embodiment of the invention.
Figure 3B:
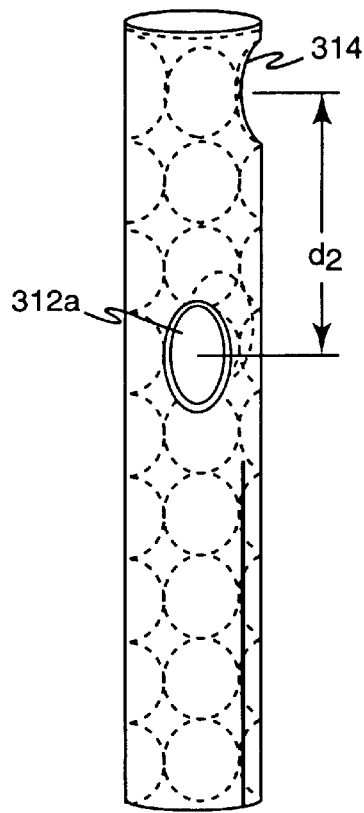
Figure 3C:
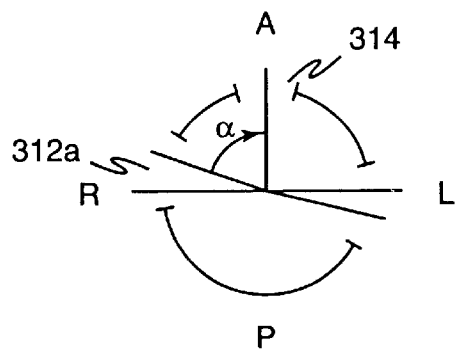

FIGS. 3A–3C illustrate an exemplary stent-graft for bridging an abdominal aortic aneurysm in which the stent-graft is adapted to press against portions of the aortic wall above the renal and the superior mesenteric artery orifices and typically below the celiac axis orifice. The example stent-graft 300 includes a main body 302 which bifurcates into a leg 304 and a stem 306 used to attach a mating leg 308 to the main body 302. The main body 302, in this case, is adapted for supra-superior mesenteric fixation and is configured to expand against portions of the aortic wall 115 above the superior mesenteric artery 108.

The main body 302 of the stent-graft 300 includes a graft material 310 and a stent system 314 which define two renal apertures 312a and 312b each being alignable with a respective one of the renal arteries when the stent-graft 300 is expanded against the aortic wall 115 and a mesenteric aperture 314 which is oriented to align with the superior mesenteric artery 110 when the stent-graft 300 is expanded against the aortic wall 115.

With the exception of its length (which is longer to accommodate the mesenteric aperture 314), the main body 302 may in general be constructed similar to the main body 202 discussed above. For example, the main body 302 may, for example, be formed from a shape memory alloy in a honeycomb shape having a number of interconnected wire loops, three of which form surrounding portions 318 which surround the renal apertures 312a and 312b and the mesenteric aperture 314.

The renal apertures 312a and 312b may, for example, be configured and oriented similar to the renal apertures 212a and 212b discussed above. The characteristics of the mesenteric aperture 314 can vary. Typically, the mesenteric aperture 314 is as large as or larger than the orifice of the mesenteric artery. Suitable sizes of the mesenteric aperture 314 range from about 1.2 to 1.5 cm or more in diameter for many applications. The orientation of the mesenteric aperture 314 relative to the renal apertures 312a and 312b can vary. Typically, the mesenteric aperture 314 is circumferentially located at an angle $\alpha$ (shown in FIG. 3C) of about 50 to 75 degrees as measured from the center right renal aperture 312a and is longitudinally located a distance $d_2$ (shown in FIG. 3B) with respect to the right renal aperture 312a of about 1.0 to 1.5 cm. The use of a mesenteric aperture 314 which is larger than the mesenteric artery orifice provides tolerance by allowing for variable sizes and orientations of the mesenteric artery 110 relative to the renal arteries 112a and 112b.

The shape of the mesenteric aperture 314 can also vary and may, for example, be rectangular, circular, or ovular. In the example embodiment, the mesenteric aperture 314 is ovular in shape and has a length in the longitudinal direction which is greater than a circumferential width. The length may range from about 1.8 to 2.0 cm and the width about 1.5 to 1.8 cm. In other embodiments, the mesenteric aperture 314 may have a length in the longitudinal direction which is less than a circumferential width.

Figure 4A:
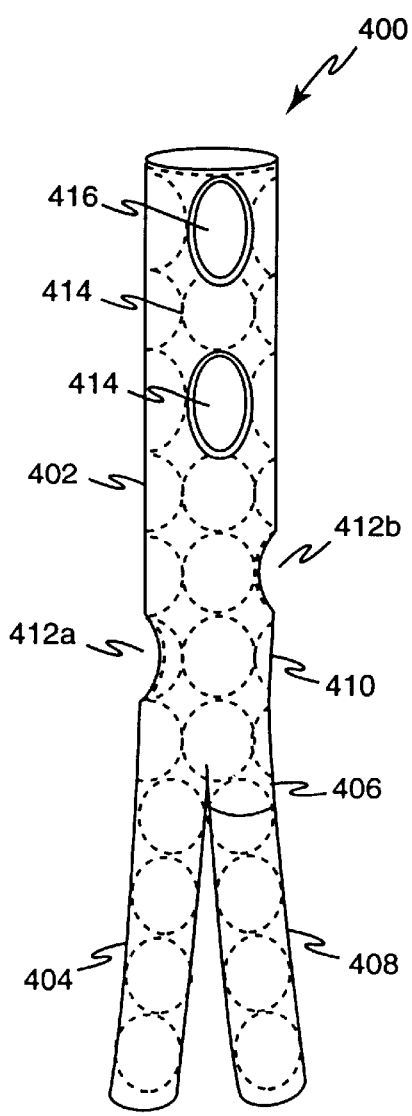
FIGS. 4A–4C illustrate an exemplary graft in accordance with another embodiment of the invention.
Figure 4B:
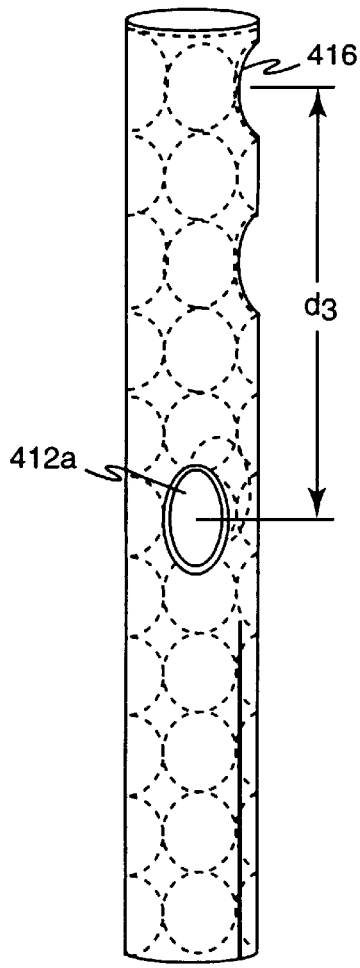
Figure 4C:
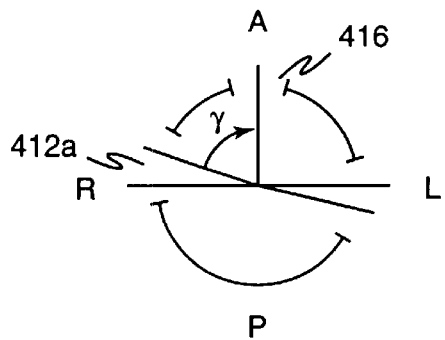

FIGS. 4A–4C illustrate an exemplary stent-graft for bridging an abdominal aortic aneurysm in which the stent-graft is configured to be positioned against a portion of the aortic wall above the renal, superior mesenteric, and celiac axis artery orifices. The example stent-graft 400 generally includes a main body 402 which bifurcates into a leg 404 and a stem 406 used to attach a mating leg 408 to the main body 402. The main body 402, in this case, is adapted for supra-celiac axis fixation and is configured to expand against portions of the aortic wall 115 above celiac axis artery 110.

The main body 402 of the stent-graft 400, like the stent-graft 300 discussed above, includes a graft material 410 and a stent system 414 which define two renal apertures 412a and 412b each being alignable with a respective one of the renal arteries when the stent-graft 400 is expanded against the aortic wall 115 and a mesenteric aperture 414 which is oriented to align with the superior mesenteric artery 108 when the stent-graft 400 is expanded against the aortic wall 115. In this case, the main body 402 further defines a celiac axis aperture 416 which is capable of aligning with the celiac axis artery 108 when the stent-graft 400 is expanded. With the exception of its length (which is longer to accommodate the celiac axis aperture 416), the main body 402 may in general be constructed similar to the main body 302 discussed above.

The renal apertures 412a and 412b as well as the mesenteric aperture 414 may, for example, be configured and oriented similar to the renal apertures 312a and 312b and mesenteric apertures 314 discussed above. The characteristics of the celiac aperture 416 can vary. Typically, the celiac aperture 416 is larger than the orifice of the celiac axis artery. Suitable sizes of the celiac aperture 416 range from about 1.2 to 1.5 cm or more in diameter for many applications. The orientation of the celiac aperture 416 relative to the other apertures can vary as well. Typically, the celiac aperture 416 is circumferentially located at an angle $\gamma$ (shown in FIG. 4C) of about 60 to 90 degrees as measured from the right renal aperture 412a. Longitudinally, the celiac aperture 416 is located a distance $d_3$ (shown in FIG. 4B) with respect to the right renal aperture 412a of about 1.5 to 2.0 cm.

Like the apertures above, the shape of the celiac aperture 416 can vary. In the example embodiment, the celiac aperture 416 is ovular in shape and has a length in the longitudinal direction which is greater than a circumferential width. For example, the length may range from about 1.8 to 2.0 cm and the width may range from about 1.5 to 1.8 cm in many applications. In other embodiments, the celiac aperture 416 may have a length in a longitudinal direction which is less than its width. While this embodiment illustrates the use of separate apertures for the celiac axis artery 108 and the superior mesenteric artery 110, in other embodiments, a single aperture may be formed to encompass both arteries 108 and 110.

While the above embodiments illustrate stent-grafts having at least two apertures (e.g., for the renal arteries), the invention is not so limited. Stent-grafts having only one aperture for bridging a defect (e.g., an aneurysm) may be formed having proximal end portions configured to be positioned against a portion of a main vessel wall above only one branch artery. Single aperture stent-grafts may be used in a variety of circumstances including, for example, bridging abdominal aortic aneurysms where the right and left renal arteries are sufficiently offset to allow the use of one renal aperture without blocking the other artery. Moreover, while the example stent-grafts shown in FIGS. 2–4 illustrate the use of bifurcated distal portions, the invention is however not limited to any particular distal portion configuration. What is important is that the proximal portion of the stent-graft include apertures capable of aligning with visceral artery orifices such that the stent-graft may be used to bridge aneurysms having minimal or no proximal neck.

Figure 5:
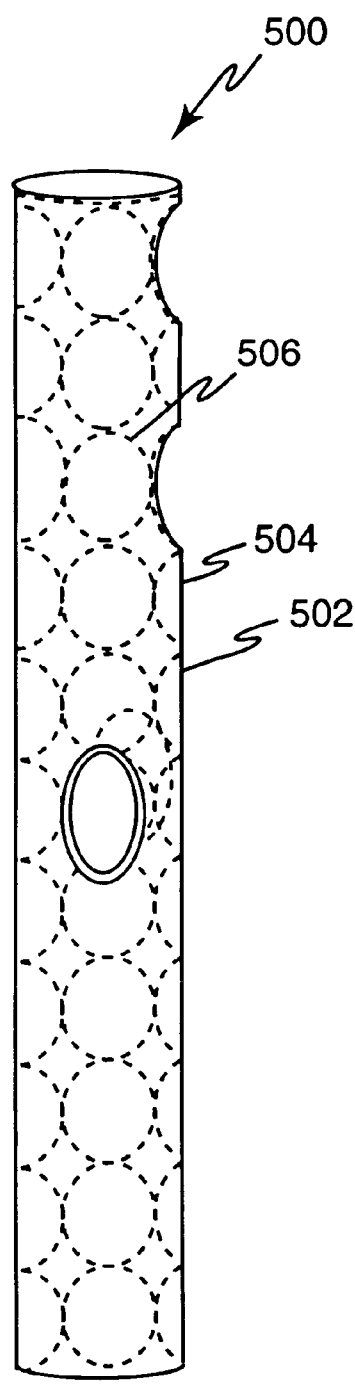
FIG. 5 illustrates an exemplary graft in accordance with yet another embodiment of the invention.
Figure 6:
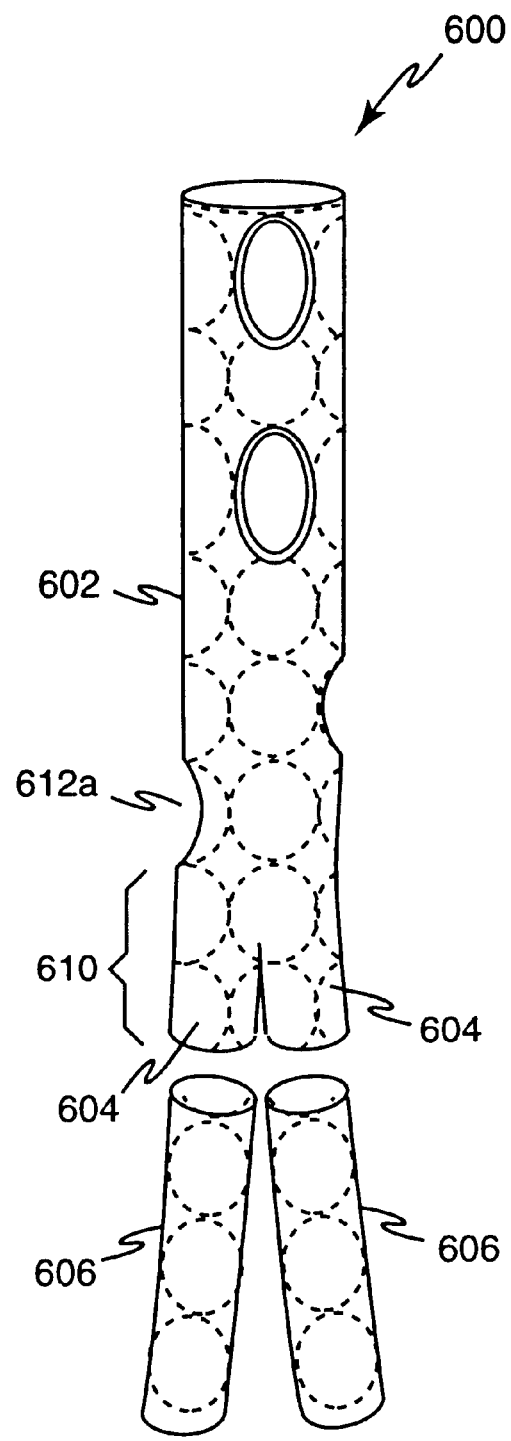
FIG. 6 illustrates an exemplary graft in accordance with still another embodiment of the invention.

FIG. 5 and 6 illustrate two alternative distal portion configurations which may be used with the invention. These exemplary, alternative distal portion configurations are depicted with proximal portions designed for supra-celiac axis fixation. It is noted, however, that similar distal configurations may be used with each of the embodiments discussed above In FIG. 5, there is illustrated a stent-graft 500 formed from a single body 502 configured to secure the proximal part of the stent-graft above the renal orifices and to secure the distal part of the stent-graft against a distal neck (e.g., between an aneurysm and the iliac bifurcation). The exemplary body 502 includes a graft material 504 supported by a stent system 506 which runs the length of the graft material 504. The body 502 may, for example, be constructed similar to those described above (e.g., Dacron™ supported by a nitinol wire mesh). Alternatively, the stent system 506 may differ from the stent systems above. For instance, the stent system 506 may include a proximal stent system (e.g., nitinol wire mesh) supporting branch artery apertures and a distal stent system (e.g., a metal spring) connected to the proximal stent system through reinforcing bars.

FIG. 6 illustrates a stent-graft 600 having bifurcated distal portion with two mating legs 606. The stent-graft includes a main body 602 having two stems 604 for attaching the legs 606. The main body 602 may be constructed similar to those described above with the exception of its lower end which includes the two stems 604 rather than a single stem and an attaching leg. The mating legs may, for example, each be constructed similar to the mating leg 208 discussed above. In the this embodiment, the stems 604 are typically sufficiently spaced from the lower aperture 612a to provide a segment 610 which may be used to retain part of the main body 602 within a sheath during deployment. Lengths of the segment 610 ranging, for example, from about 2 to 3 cm would be suitable for many applications.

Using the above grafts, defects such as abdominal aortic aneurysms may be more effectively bridged than compared to conventional techniques. In particular, by providing a graft which can be disposed against portions of the aortic wall above the renal arteries (and, if desired, above the superior mesenteric or celiac axis arteries), aortic aneurysms having minimal or no necks can, for example, be excluded without obstructing blood flow through the renal arteries. Additionally, by providing apertures having areas as large as or larger than the respective branch artery orifices, positioning of the graft within an aorta is facilitated.

It is stressed that the sizes, shapes and orientations of the various apertures discussed in the embodiments above are provided by way of example only and are not intended to limit the scope of the invention. Indeed, it is contemplated that a number of different grafts having apertures of different sizes, shapes and/or orientations will be made in order to accommodate variations in the size, shape and location of the renal, superior mesenteric and/or celiac axis orifices of different patients.

FIGS. 7A–7D illustrate an exemplary process for bridging an abdominal aortic aneurysm having minimal or no neck. By way of example and not of limitation, the exemplary process will be illustrated using a stent-graft similar to that depicted in FIGS. 4A–4C above. A similar process may be employed to bridge abdominal aortic aneurysms using the other stent-grafts discussed above.

Figure 7A:
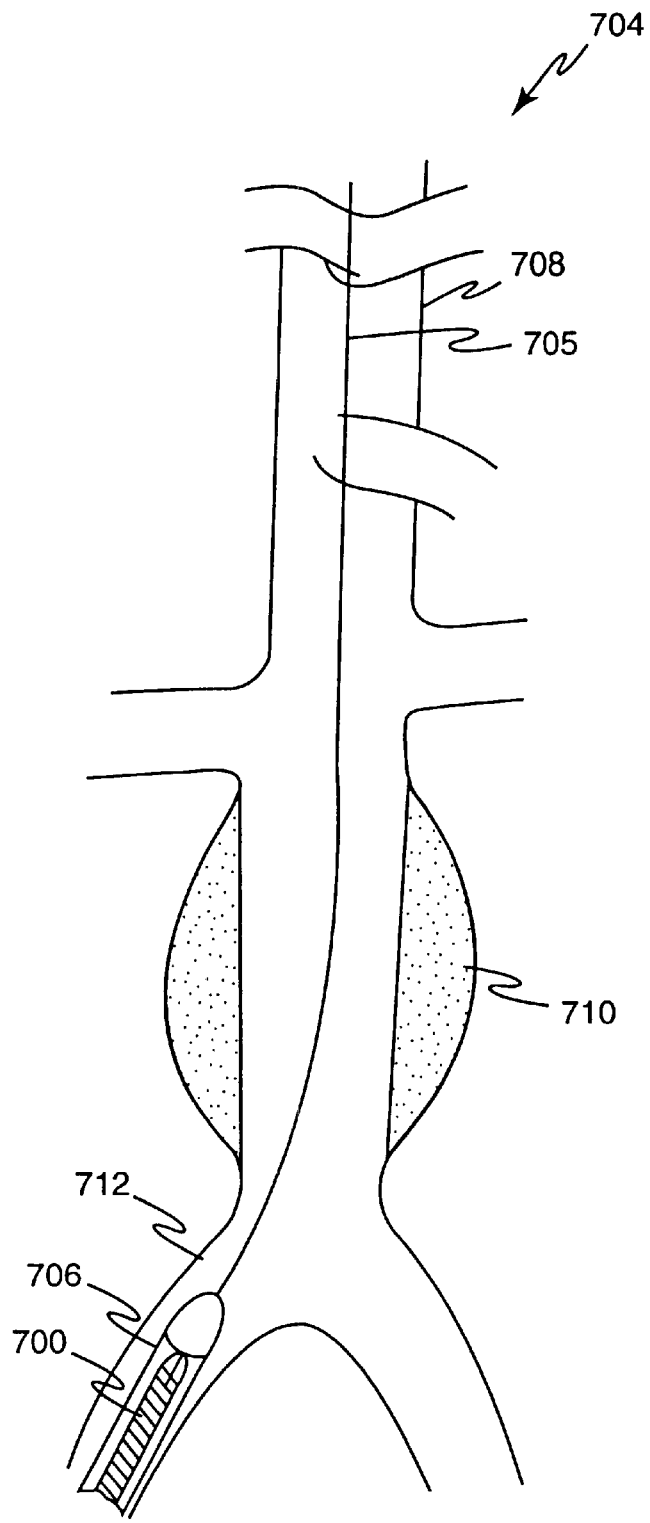
FIGS. 7A–7D illustrate an exemplary process for deploying a graft in accordance with one embodiment of the invention.

Consistent with the exemplary process, a main body 700 of the stent-graft is inserted within the vascular system 704 in a contracted state and typically over a guidewire 705. This typically involves placing the main stent-graft body 700 within a sheath 706, introducing the sheath 706 and the main body 700 into the vascular system 704 at an access site (not shown) and advancing the sheath 706 and main body 700 through the vascular system 704 toward the abdominal aortic aneurysm 710. FIG. 7A illustrates a view of the sheath 706 and main stent-graft body 700 within an iliac artery 712 as it is advanced toward the abdominal aortic aneurysm 710. In the example embodiment, a balloon catheter is also disposed in the sheath 706 within the main stent-graft body 700. The balloon catheter will be used to partially expand the main stent-graft body 700 as will be discussed below.

Optionally, prior to initial deployment of the main stent-graft body 700, the various visceral artery orifices may be marked to facilitate alignment of the main body 700 with the orifices. Marking of the renal orifices may be performed by, for example, placing a 0.014 to 0.018 inch platinum tip guide wire into each of the visceral arteries using well-known techniques.

Figure 7B:
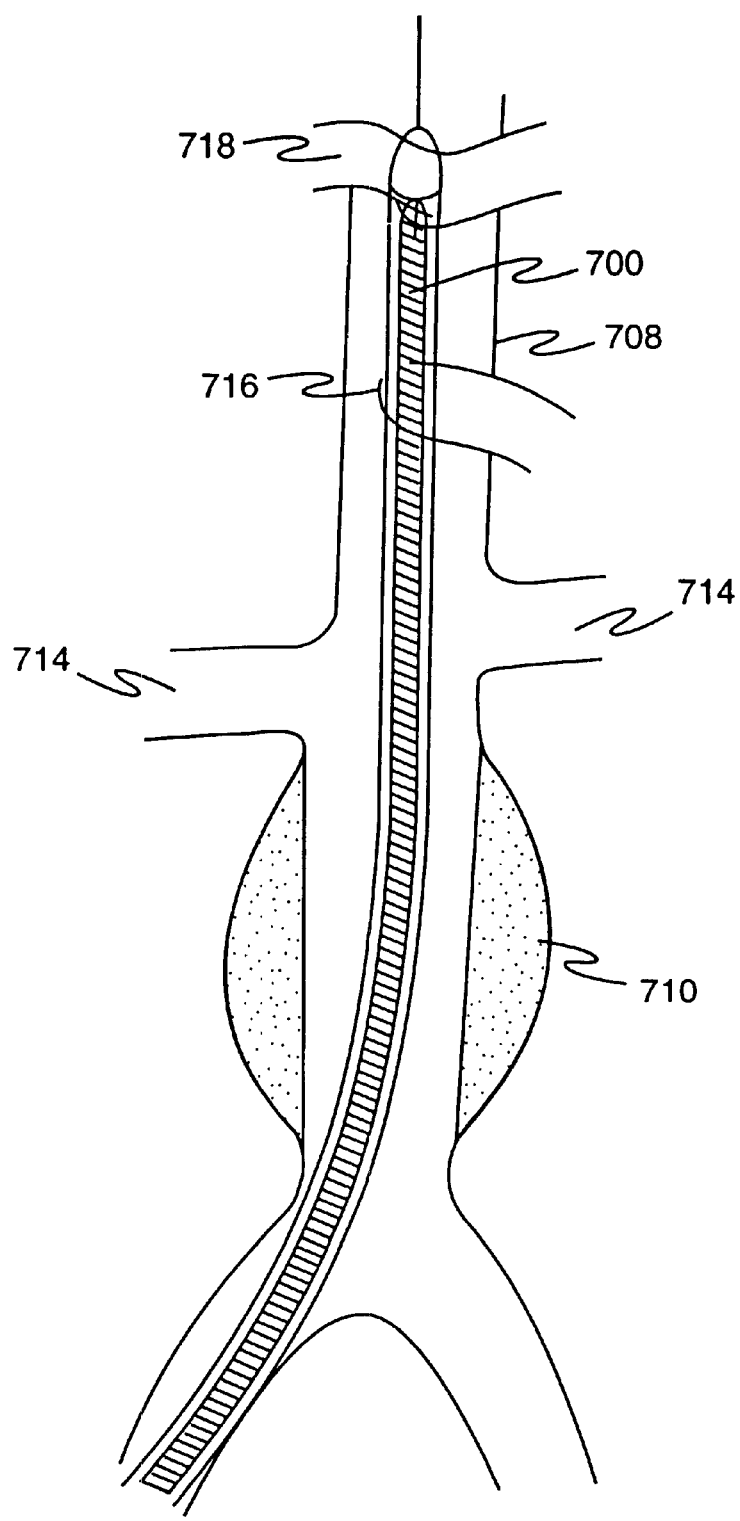

The main stent-graft body 700 is then advanced to the abdominal aortic aneurysm 710, as illustrated in FIG. 7B. This typically includes preliminary positioning the sheathed main body 700 within the aorta 708 such that each aperture 702 approximately aligns with a respective one of the branch artery orifices 714–718. The main stent-graft body 700 may be positioned within the aorta 708 in a variety of manners, using a number of different imaging techniques including, for example, single-plane or bi-plane fluoroscopy and/or three dimensional imaging.

Using fluoroscopy, for example, radiopaque aperture markers and a radiopaque aligning system (e.g., a ◇-| aligning system) may be employed to axially and radially align the apertures 702 with the visceral orifices. Using this technique, an angiogram may first be developed to relate the visceral arteries to the spine or a radiopaque ruler. The alignment of the apertures 702 may then be related to the spine or ruler using the angiogram.

Using three-dimensional imaging, the main stent-graft body 700 may be viewed from desired angles to position the main body 700. While an aligning system would not be necessary, radiopaque aperture makers may be used to facilitate alignment using three-dimensional imaging. With this technique, a three-dimensional imaging program using computed tomography (CT), such as 3DVirtuoso from Siemens AG, Medical Engineering, Computed Tomography, Forchheim Germany, Vitrea, from Vital Images, Inc., Minneapolis, Minn., or GENavigator from GE Medical Systems may be used.

Figure 7C:
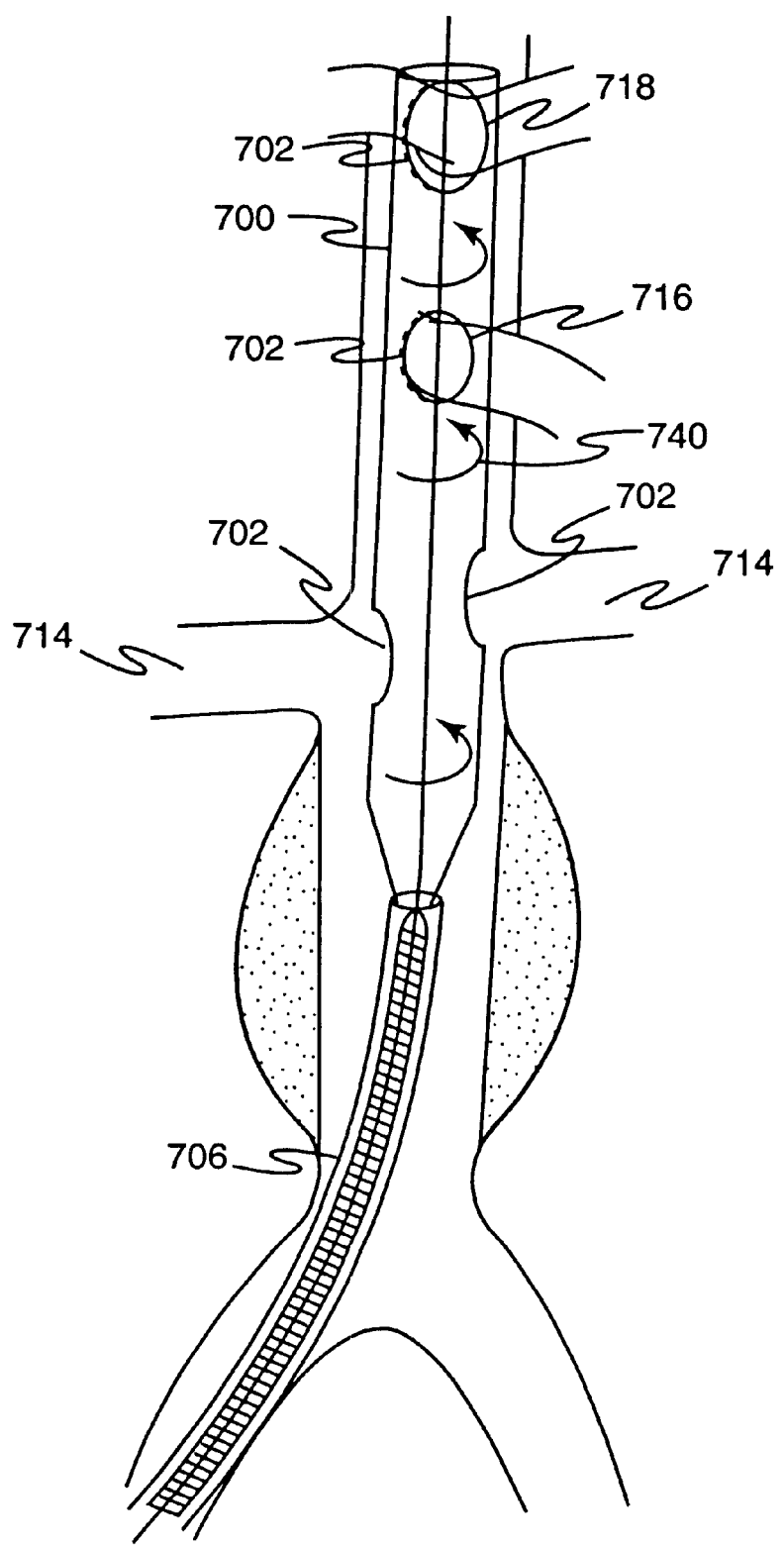

The main stent-graft body 700 is then partially expanded and the positioning of the main stent-graft body 700 is adjusted, if needed, in order to align the apertures 702 with the branch artery orifices 714–718. FIG. 7C is a typical view of the main stent-graft body 700 when partially expanded. The manner in which the main stent-graft body 700 is partially expanded varies with the shape-memory characteristics of stent system used. For instance, using a main stent-graft body 700 having a stent-system with an AF temperature at or below body temperature, partial expansion may, for example, be performed by withdrawing the sheath 706 to expose the apertures and expanding the exposed section of the main stent-graft body 700 using a water-cooled balloon which maintains the stent-graft at a temperature below the AF temperature. In this manner, the balloon by virtue of the cool water (illustrated by arrows 740) prevents the exposed section of the main stent-graft body 700 from fully expanding and, at the same time, forcibly expands the main stent-graft body 700 from its martensite shape.

Positioning and alignment of the main stent-graft body 700 while partially expanded may, for example, be performed using, for example, single or bi-plane fluoroscopy or three dimensional imaging as discussed above. Advantageously, a lower section of the main stent-graft body 700 is kept within the sheath 706 to facilitate rotational alignment of the main stent-graft body 700 while partially expanded.

The main stent-graft body 700 is then expanded to its expanded state such that the apertures 702 align with the visceral artery orifices 714–718 and the main stent-graft body 700 presses against the aortic wall. The main stent-graft body 700 may be expanded using a variety of techniques typically dependent on the shape memory characteristics of stent-graft used. With the a main stent-graft body having an AF temperature at or below body temperature, as discussed above, the main body 700 is typically expanded by withdrawing the cooled water and heating the stent system. The stent system may, for example, be heated by the patient body itself and/or using external heating means (e.g., an electrical current).

After expanding the exposed section of main stent-graft body 700 against the aortic wall, a final inspection may be performed using, for example, fluoroscopy or three dimensional imaging, to insure proper location of the exposed part of the main stent-graft body 700. Should the main stent-graft body 700 need repositioning, the main stent-graft body 700 may be contracted and repositioning until proper positioning of the main stent-graft body 700 is achieved. For example, using a two-way shape memory stent system, contraction of the main stent-graft body 700 may simply be accomplished by cooling the stent system (e.g., by flowing cool water through the balloon) below its MS temperature to suitably contract the main stent-graft body 700. Using a one-way, shape memory stent system, contraction may, for example, be accomplished by cooling and resheathing the exposed section of the main stent-graft body 700. In both cases, the exposed stent-graft section may be sheathed while cooling to insulate the patient's body from the effects of the cooling. Repositioning after contraction may be performed by as discussed above.

Figure 7D:
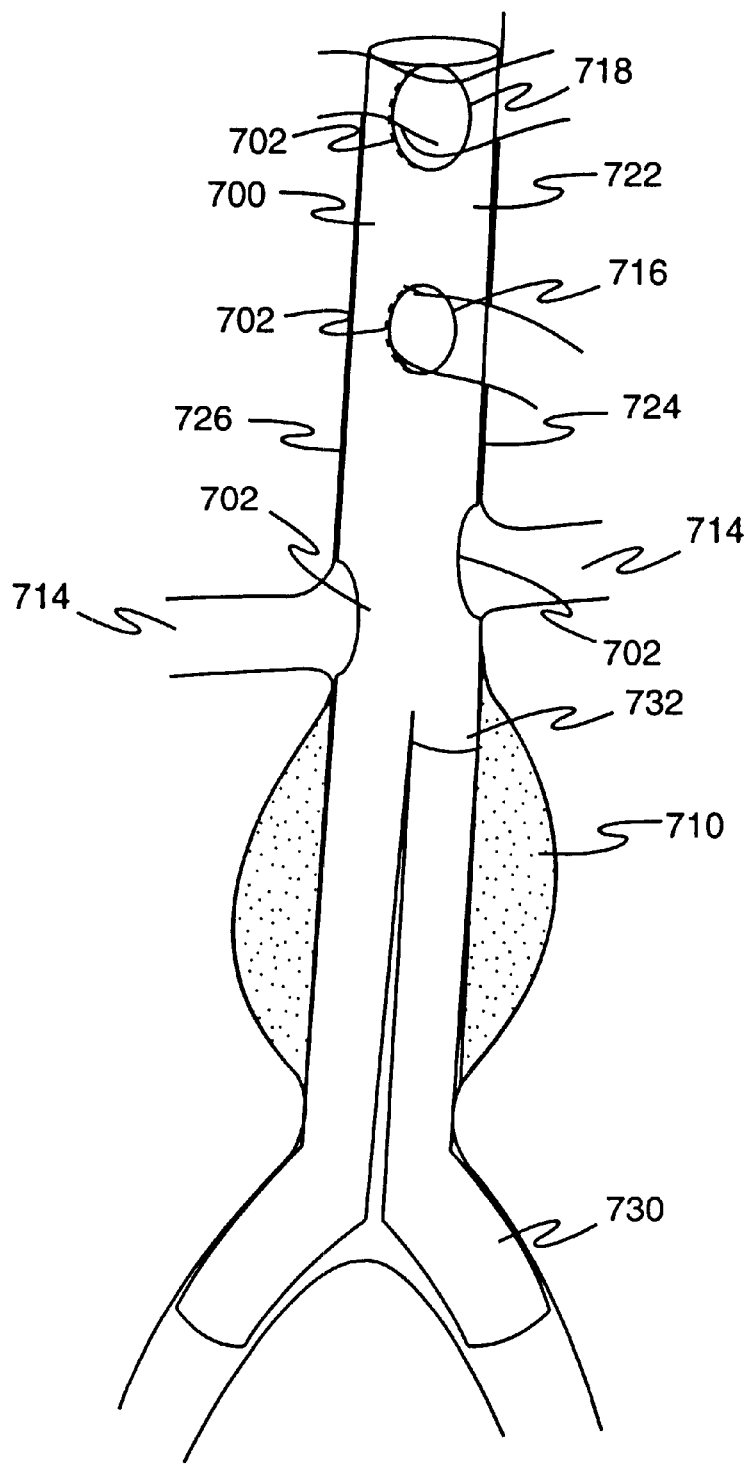

Once the exposed section of the main stent-graft body 700 is properly positioned, the remaining, sheathed section of the main stent-graft body 700 is then exposed and fully expanded, for example, by body heat and/or external heating means. The mating leg 730 then attached to the main body 700 of the stent graft. Typically, this includes sheathing the leg and advancing the sheathed leg into a stem 732 of the main body 700. The sheath is then withdrawn and the leg 730 expanded against the stem 732 for retention. FIG. 7D illustrates a typical position of the stent-graft after full deployment. In particular, the main stent-graft body 700 presses against portions 724 and 726 of the aortic wall above the two renal artery orifices 714 (and in this case, above the superior mesenteric and celiac axis orifices 716 and 718) and the apertures 702 of the main stent-graft body 700 are positioned so that the branch artery orifices 714–718 typically lie within the apertures 702. Advantageously, the proximal end 722 of the main stent-graft body 700 sealingly engages the aortic wall without need of an aneurysm neck (i.e., patent portions of the aortic wall between the renal artery orifices 714 and the aneurysm 710), while portions of the stent system surrounding the apertures 702 provide adequate sealing around the branch artery orifices 714–718.

As noted above, partial expansion and full expansion of the main stent-graft body 700 can vary with the type of stent system used. Using, for example, a main stent-graft body 700 having a stent-system with an AF temperature greater than body temperature (e.g. about 48° C.), partial expansion of the main stent-graft body 700 can be performed by partially withdrawing the sheath 706 and heating the stent system to a temperature between its AS and AF temperatures, thereby partial expanding the stent system through partial recovery of its austenite form. The heating may be performed using body heat alone or external means depending on the AS temperature of the stent system. For example, if the AS temperature is below body temperature, body heat alone may be used. If the AS temperature is above body temperature, some external heating is used.

The main stent-graft body 700 may then be fully expanded to its expanded state by heating the stent-graft through its AF temperature. This may, for example, be done using, for example, known external heating means. In this case, it is noted that the temperature of the main stent-graft body 700 will retreat to body temperature after removal of the external heat. However, the main stent-graft body 700 can remain in its expanded (e.g., austenite) state rather than transform to a contracted (e.g., martensite) state due to, for example, transformation hysteris.

Using the above process, a graft for bridging an abdominal aortic aneurysm can be efficiently positioned above the renal arteries (and if desired, above the celiac axis or superior mesenteric arteries) without obstructing the blood flow through the arteries. The realignment of the apertures is particularly beneficial when aligning grafts having apertures for two or more vessels, such as grafts which have renal apertures and apertures for the mesenteric and/or celiac arteries.

Figure 8:
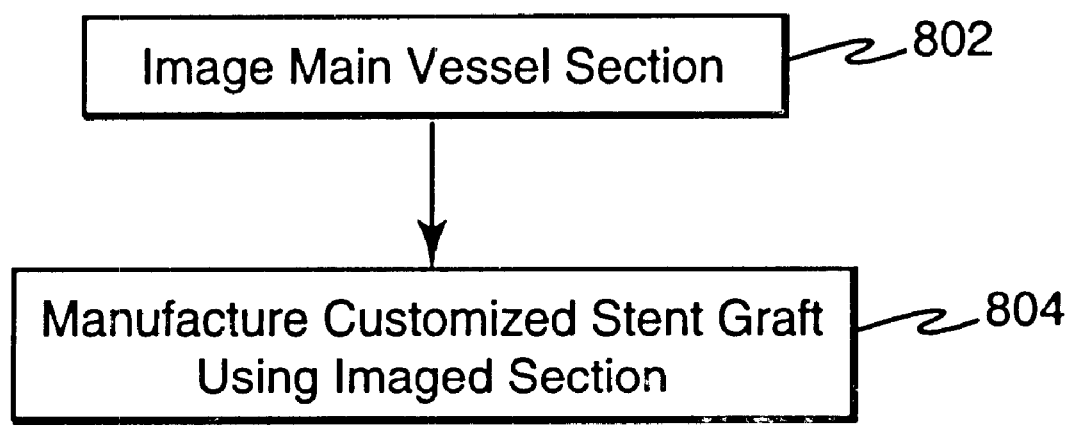
FIG. 8 is a flow chart illustrating an exemplary manufacturing process in accordance with an embodiment of the invention.

FIG. 8 is a flow chart illustrating an exemplary process for making a customized stent-graft for bridging a defect (e.g., an aneurysm) disposed in a main vessel near one or more branch vessels extending from the main vessel. In accordance with this process, a three dimensional image of interior of the main vessel near the one or more branch vessels is developed prior to forming the stent-graft, as illustrated at block 802. This typically involve using three dimensional imaging to reconstruct the interior portion of the main vessel, including the location and size of each of the one or more branch vessels. Three dimensional reconstruction may by performed by exposing the relevant section of the main vessel and constructing a three dimensional image of the vessel section using the exposed images. This may be performed using, for example, a CT scanner and three dimensional imaging system, such as 3DVirtuoso, Vitea, or GENavigator.

Using the three dimensional image, a customized stent-graft is formed, as indicated in block 804. The customized stent-graft generally includes one or more apertures each disposed on the stent-graft such that it aligns with a corresponding one or more of the branch vessels. The customized stent-graft can be formed using the three-dimensional reconstruction using a number of different techniques. For example, the 3D reconstruction may be translated to a CAD program which in turn is used to manufacture the graft. This translation may, for example, be done using the CT-Modeller System from Materialise N. V., Belgium.

Using the above process, a stent-graft for bridging a defect, such as an abdominal aortic aneurysm having minimal or no proximal neck, may be customized to the patient. In particular, the apertures in stent-graft for renal arteries (and if desired, apertures for the mesenteric and/or celiac arteries) may be customizably formed in the graft material of the stent-graft using a three dimensional reconstruction of the interior of the aorta around the renal arteries (and in the optional cases the mesenteric and celiac arteries). A customized stent-graft may be particularly advantageous when it is desired to bridge an abdominal aortic aneurysm of a patient having an abnormal aortic profile (e.g., abnormal size or orientation of branch vessels, more than two renal arteries, etc.).

As noted above, the present invention is generally directed to grafts for bridging defects in main vessels near one or more branch vessels. The type of defect as well as the vessel in which the defect resides can vary. Accordingly, the present invention should not be considered limited to the particular examples described above, but rather should be understood to cover all aspects of the invention as fairly set out in the attached claims. Various modifications, equivalent processes, as well as numerous structures to which the conventional invention may be applicable will be readily apparent to those of skill in the art to which the present invention is directed upon review of the present specification. The claims are intended to cover such modifications and devices.

What is claimed is:

1. A stent-graft for bridging an aneurysm in an aorta, the aneurysm being at least partially disposed between two renal arteries and two iliac arteries, comprising:
   a graft material defining two renal apertures each oriented to align with one of the two renal arteries when the stent-graft is in an expanded state; and
   a stent system for supporting the graft material in a contracted state wherein each renal aperture is contracted and the expanded state wherein each renal aperture is expanded;
   wherein the stent system, when in the expanded state, is adapted to press against a portion of the aortic wall above the first renal artery and against a portion of the aortic wall above the second renal artery;
   wherein the graft material defines a mesenteric aperture oriented to align with a superior mesenteric artery when the stent-graft is in an expanded state.

2. The stent-graft of claim 1, wherein the stent system supports the mesenteric aperture and when in the expanded state, is adapted to press against a portion of the aortic wall above the superior mesenteric artery.

3. The stent-graft of claim 2, wherein the graft material defines a celiac aperture oriented to align with a celiac axis artery when the stent-graft is in the expanded state.

4. The stent-graft of claim 3, wherein the stent system supports the celiac aperture and when in the expanded state, is adapted to press against a portion of the inner wall of the aorta above the celiac axis artery.

5. A process of bridging a defect disposed in a main vessel near one or more branch vessels, comprising:
   using three dimensional imaging, positioning, within the main vessel, a contracted graft having a sidewall defining one or more apertures;
   using three dimensional imaging, aligning the graft within the main vessel such that each aperture aligns with at least a respective one of the branch vessels; and
   expanding the graft to an expanded state wherein the one or more apertures are aligned with the one or more branch vessels and the graft presses against a wall of the main vessel.

6. The process of claim 5, wherein aligning the graft includes partially expanding the graft and rotating the graft while partially expanded about its longitudinal axis to align the one or more apertures in the sidewall of the graft with the one or more branch vessels.

7. The process of claim 5, wherein the main vessel is an aorta and the defect is an aneurysm.

8. A process of bridging a defect disposed in a main vessel near one or more branch vessels, comprising:
   inserting, within the main vessel, a graft in a contracted state, the graft defining one or more apertures;
   aligning the graft within the main vessel such that each aperture aligns with at least a respective one of the branch vessels; and
   expanding the graft to an expanded state wherein the one or more apertures are aligned with the one or more branch vessels and the graft presses against a wall of the main vessel;
   wherein aligning the graft includes partially expanding the graft and aligning the graft while partially expanded;
   wherein partially expanding the graft includes maintaining the graft in at least a partial martensite phase while forcibly expanding the graft.

9. The process of claim 8, wherein aligning includes using three-dimensional imaging.

10. The process of claim 8, wherein aligning the graft includes partially expanding the graft and rotating the graft, while partially expanded, about its longitudinal axis to align the one or more apertures of the graft with the one or more branch vessels, the apertures being defined in a sidewall of the graft.

11. A process of bridging a defect disposed in a main vessel near one or more branch vessels, comprising:
   inserting, within the main vessel, a graft in a contracted state, the graft defining one or more apertures;
   aligning the graft within the main vessel such that each aperture aligns with at least a respective one of the branch vessels; and
   expanding the graft to an expanded state wherein the one or more apertures are aligned with the one or more branch vessels and the graft presses against a wall of the main vessel;
   wherein aligning the graft includes partially expanding the graft and aligning the graft while partially expanded;
   wherein partially expanding the graft includes heating the stent to a temperature between an austenite start temperature and an austenite finish temperature of the graft.

12. The process of claim 11, wherein aligning includes using three-dimensional imaging.

13. The process of claim 11, wherein aligning the graft includes partially expanding the graft and rotating the graft, while partially expanded, about its longitudinal axis to align the one or more apertures of the graft with the one or more branch vessels, the apertures being defined in a sidewall the graft.

14. A stent-graft for bridging an aneurysm in an aorta, the aneurysm being at least partially disposed between two renal arteries and two iliac arteries, comprising:

a graft material defining at least one renal aperture oriented to align with one of the two renal arteries when the stent-graft is in an expanded state; and a stent system for supporting the graft material in a contracted state wherein each renal aperture is contracted and the expanded state wherein each renal aperture is expanded;

further including a radiopaque marker surrounding the perimeter of a respective renal aperture.

15. A stent-graft for bridging an aneurysm in an aorta, the aneurysm being at least partially disposed between two renal arteries and two iliac arteries, comprising:

a graft material defining at least one renal aperture oriented to align with one of the two renal arteries when the stent-graft is in an expanded state; and a stent system for supporting the graft material in a contracted state wherein each renal aperture is contracted and the expanded state wherein each renal aperture is expanded;

wherein each renal aperture is larger than the orifice of the respective renal artery.

16. A graft for bridging an aneurysm at least partially disposed in an aorta between two renal arteries and two iliac arteries, comprising:

graft material adapted to extend from above at least one of the two renal arteries to a region below the aneurysm without substantially extending into the either of the two renal arteries; and at least one renal aperture defined by the graft material for aligning with a respective one of the two renal arteries; and a stent system attached to the graft material;

wherein the graft material is adapted to expand from a contracted state wherein the at least one renal aperture is contracted and an expanded state wherein the at least one renal aperture is expanded and the graft material presses against a wall of the aorta;

wherein the at least one renal aperture, defines an opening larger than an orifice of the respective renal artery so as not to obstruct the respective renal artery when the graft material is in the expanded state.

17. The graft of claim 16, wherein the graft material defines a unitary tubular member adapted to extend from above at least one of the two renal arteries to the region below the aneurysm without substantially extending into the either of the two renal arteries.

18. The graft of claim 16, wherein the stent system further defines at least one aperture aligned with the at least one renal aperture defined by the graft material.

19. A stent-graft for bridging an aortic aneurysm at least partially disposed between two renal arteries and two iliac arteries, comprising:

a stent system; and a unitary piece of graft material attached to the stent system and adapted to extend from above at least one of the two renal arteries to a location near the distal end of the aneurysm, the graft material defining at least one renal aperture for aligning with a respective one of the two renal arteries;

wherein the at least one renal aperture is contracted when the graft material is in a contracted state and wherein the at least one renal aperture is expanded when the graft material is an expanded state; wherein the at least one renal aperture in the expanded state defines an opening larger than an orifice of the respective one of the two renal arteries.

20. The stent-graft of claim 19, wherein the at least one renal aperture includes a single renal aperture and the unitary piece of graft material includes a first end adapted to be located between the two renal arteries and a second end adapted to be located near the distal end of the aneurysm.

21. The stent-graft of claim 19, wherein the at least one renal aperture includes two renal apertures and the unitary piece of graft material is adapted to extend from a location above the two renal arteries to the location near the distal region of the aneurysm.

22. The stent-graft of claim 19, wherein the stent system includes at least one supporting portion attached to the graft material surrounding the perimeter of the at least one renal aperture.

23. The graft of claim 19, wherein the unitary piece of graft material is adapted to extend from above at least one of the two renal arteries to the location near the distal end of the aneurysm without substantially extending into the either of the two renal arteries.

* * * * *

(12) EX PARTE REEXAMINATION CERTIFICATE (7674th)
United States Patent
Castaneda

(10) Number: US 6,395,018 C1
(45) Certificate Issued: Aug. 10, 2010

(54) ENDOVASCULAR GRAFT AND PROCESS FOR BRIDGING A DEFECT IN A MAIN VESSEL NEAR ONE OF MORE BRANCH VESSELS

(75) Inventor: Wilfrido R. Castaneda, New Orleans, LA (US)

(73) Assignee: Envatech, LLC, Edina, MN (US)

Reexamination Request:
No. 90/009,405, Feb. 17, 2009

Reexamination Certificate for:
Patent No.: 6,395,018
Issued: May 28, 2002
Appl. No.: 09/020,869
Filed: Feb. 9, 1998

(51) Int. Cl.
    *A61F 2/00* (2006.01)

(52) U.S. Cl. .................................. 623/1.13; 623/1.35
(58) Field of Classification Search .................. None
    See application file for complete search history.

(56) References Cited

U.S. PATENT DOCUMENTS

| 5,489,295 A | * | 2/1996 | Piplani et al. ............... 623/1.35 |
| 5,653,743 A | | 8/1997 | Martin |
| 5,709,713 A | | 1/1998 | Evans et al. |
| 5,984,955 A | | 11/1999 | Wisselink |
| 6,030,414 A | | 2/2000 | Taheri |
| 6,352,561 B1 | | 3/2002 | Leopold et al. |
| 6,524,335 B1 | | 2/2003 | Hartley et al. |

OTHER PUBLICATIONS

Jae Hyung Park, MD, et al., Fenestrated Stent–Grafts for Preserving Visceral Arterial Branches in the Treatment of Abdominal Aortic Aneurysms: Preliminary Experience, Journal of Vascular Interventional Radiology, Nov.–Dec. 1996, 7(6), pp. 819–823.

* cited by examiner

*Primary Examiner*—Cary E. O'Connor

(57) ABSTRACT

An endovascular graft for bridging a defect in a main vessel near one or more branch vessels is provided. A graft, consistent with one embodiment of the invention, includes a tubular member which defines one or more apertures and is adapted for expansion against inner wall of a main vessel above one or more branch vessels. Each aperture defined by the tubular member is alignable with at least one of the one or more branch vessels and may have an area which is as large as or larger than the opening of the respective branch vessel(s) when the tubular member is expanded against the inner wall of the main vessel. Embodiments of the invention are particularly suited for bridging abdominal aortic aneurysms having short or no proximal necks, a significant factor limiting the use of conventional grafts for bridging abdominal aortic aneurysms.

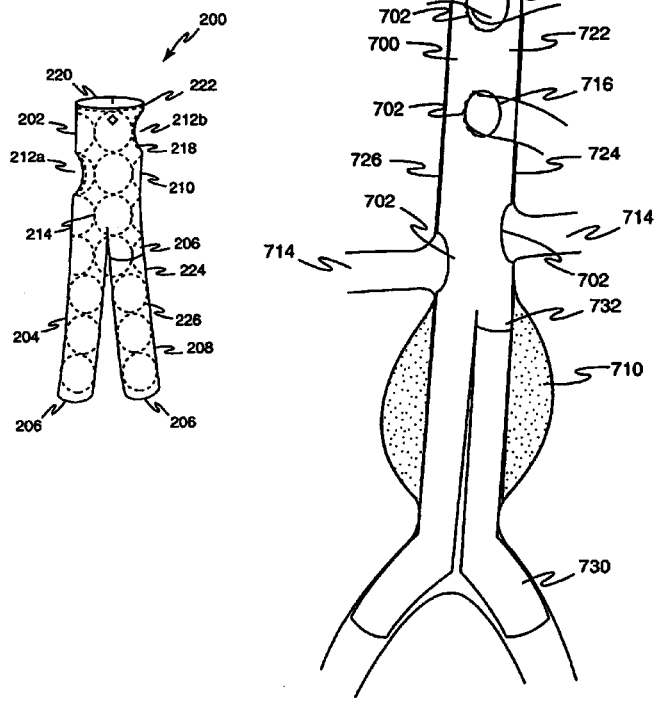

US 6,395,018 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-4 and 14-23 are cancelled.

New claims 28-46 are added and determined to be patentable.

Claims 5-13 were not reexamined.

*24. A graft system for bridging an aneurysm at least partially disposed in an aorta between two renal arteries and two iliac arteries, comprising:*
  *a stent-graft including:*
    *graft material adapted to extend from above at least one of the two renal arteries to a region below the aneurysm without substantially extending into the either of the two renal arteries; and*
    *at least one renal aperture defined by the graft material for aligning with a respective one of the two renal arteries; and*
    *a stent system attached to the graft material;*
  *wherein the graft material is adapted to expand from a contracted state wherein the at least one renal aperture is contracted and an expanded state wherein the at least one renal aperture is expanded and the graft material presses against a wall of the aorta;*
  *wherein the at least one renal aperture, defines an opening larger than an orifice of the respective renal artery so as not to obstruct the respective renal artery when the graft material is in the expanded state;*
  *a delivery system operable with the stent-graft to partially expand at least a section of the stent-graft including the renal aperture and to advance and rotate the partially expanded section of the stent-graft while the renal aperture is partially expanded for aligning the renal aperture with its respective artery and;*
  *wherein the stent-graft further includes an upper section and a lower section, the upper section of the stent-graft including an upper part of the stent system, an upper part of the graft material and the renal aperture, the upper section being adapted to extend from above the aneurysm to a region within the aneurysm above an iliac artery; the lower section including a lower part of the stent system and a lower part of the graft material and being adapted to extend from the upper section of graft material into one or both iliac arteries, the delivery system being operable with the upper section of the stent-graft to partially expand, advance and rotate the upper section of the stent-graft prior to expansion of the lower section of the stent-graft.*

*25. The graft system of claim 24, wherein the delivery system includes an elongated member coupled to the upper section of the stent-graft and extending into the vascular system, the elongated member being capable of rotating and advancing the upper section of the stent-graft.*

*26. The graft system of claim 25, wherein the elongated member includes a sheath.*

*27. The graft system of claim 24, wherein the delivery system includes a sheath housing the upper section of the stent-graft during delivery and being capable of withdrawal from about the upper section for partial expansion of the upper section of the stent-graft.*

*28. The graft system of claim 27, wherein the delivery system includes a balloon for expanding the upper section of the stent-graft.*

*29. The graft system of claim 24, wherein the upper section of the stent-graft includes a radiopaque marking system having a first component with one or more markers for indicating the position of the renal apertures and a second component with one or more markers for indicating the orientation of the partially expanded, upper section of the stent-graft.*

*30. The graft system of claim of claim 29, wherein at least one of the second component markers is located on the stent-graft between an upper end of the stent-graft and a lowermost edge of an uppermost renal aperture.*

*31. The graft system of claim 24, wherein the graft material defines two renal apertures each having a different shape.*

*32. A method of deploying a graft for bridging an aneurysm at least partially disposed in an aorta between two renal arteries and two iliac arteries, the graft comprising:*
  *a stent-graft including:*
    *graft material adapted to extend from above at least one of the two renal arteries to a region below the aneurysm without substantially extending into the either of the two renal arteries; and*
    *at least one renal aperture defined by the graft material for aligning with a respective one of the two renal arteries; and*
    *a stent system attached to the graft material;*
  *wherein the graft material is adapted to expand from a contracted state wherein the at least one renal aperture is contracted and an expanded state wherein the at least one renal aperture is expanded and the graft material presses against a wall of the aorta;*
  *wherein the at least one renal aperture, defines an opening larger than an orifice of the respective renal artery so as not to obstruct the respective renal artery when the graft material is in the expaned state; and*
  *the method comprising:*
    *advancing at least a first section of the stent-graft including the renal aperture within the vascular system to position the first section of the stent-graft within the aorta at the location of the aneurysm;*
    *adjusting the position of the first section of the stent-graft by partially expanding the first section of the stent-graft and moving the first section of the stent-graft in the direction of its axis and rotating the first section of the stent-graft about its axis; and*
    *after adjusting the position of the first section of the stent-graft, positioning the first section of the stent-graft against the wall of the aorta by further expanding the first section of the stent-graft.*

*33. The method of claim 32, wherein:*
  *the first section of the stent-graft includes a radiopaque marking system having first and second components; and*
  *adjusting includes adjusting the first section of the stent-graft while partially expanded by moving the first sec-* tion along its axis with reference to the first component of the marking system and rotating the first section about its axis with reference to the second component of the marking system.

34. The method of claim 32, wherein:
advancing includes advancing the first section of the stent-graft within the aorta so that the renal aperture and adjacent parts of the graft material and stent system, located above a bottom of the renal aperture, lie above the proximal portion of the aneurysm;
positioning the first section of the stent-graft includes positioning the renal aperture and adjacent parts of the graft material and stent system entirely above the proximal portion of the aneurysm when fully expanded.

35. The method of claim 32, wherein the at least one renal aperture includes two renal apertures, wherein:
advancing includes advancing the first section of the stent-graft within the aorta so that the two renal apertures and adjacent parts of the graft material and stent system, located above a bottom of a lowermost one of the two renal apertures, lie above the proximal portion of the aneurysm;
positioning the first section of the stent-graft includes positioning the two renal apertures and adjacent parts of the graft material and stent system entirely above the proximal portion of the aneurysm when fully expanded.

36. The method of claim 32, wherein adjusting includes withdrawing a sheath from part of the stent-graft while retaining part of the stent-graft within the sheath.

37. The method of claim 32 further comprising deploying a lower part of the stent-graft after deploying an upper part of the stent-graft, the lower part of the stent-graft adapted to extend from the upper part of the stent-graft to a region below the aneurysm.

38. A method of deploying a stent-graft for bridging an aneurysm in an aorta, the aneurysm being at least partially disposed between two renal arteries and two iliac arteries, the stent graft comprising:
a graft material including an upper section and a lower section, the upper section of graft material being adapted to extend from above the aneurysm to a region within the aneurysm above an iliac artery and the lower section of the graft material being adapted to extend from the upper section of graft material into one or both iliac arteries, the upper section of the graft material defining at least one renal aperture oriented to align with one of the two renal arteries when the stent-graft is in an expanded state; and
a stent system for supporting the graft material in a contracted state wherein each renal aperture is contracted and the expanded state wherein each renal aperture is expanded, wherein each renal aperture is larger than the orifice of the respective renal artery, the stent system including an upper part associated with the upper section of graft material and a lower part associated with the lower section of graft material, wherein the upper section of graft material and upper part of the stent system form an upper part of the stent-graft and wherein the lower section of graft material and lower part of the stent system form a lower part of the stent-graft; and
the method comprising:
deploying the upper part of the stent-graft from above a renal artery to a region within the aneurysm above an iliac artery by:
preliminarily positioning the upper part of the stent-graft at the location of the aneurysm by advancing the upper part of the stent-graft through the vascular system;
partially expanding the upper part of the stent-graft by withdrawing a sheath from about the upper part of the stent-graft after preliminarily positioning the upper part of the stent-graft;
adjusting the position of the upper part of the stent-graft while partially expanded by axially and radially aligning the renal aperture with respective renal artery; and
positioning the upper part of the stent-graft against a vessel wall by further expanding the upper part of the stent-graft after adjusting the position of the upper part of the stent-graft; and
after deploying the upper part of the stent-graft, deploying the lower part of the stent-graft from the upper part of the stent-graft into one or both iliac arteries in order to bridge the aneurysm.

39. The method of claim 38, wherein partially expanding by withdrawing the sheath includes withdrawing the sheath to expose the renal aperture, a first set of one or more markers for indicating the position of the renal aperture and a second set of one or more markers for indicating the orientation of the upper part of the stent-graft; wherein adjusting includes adjusting the position of the renal aperture and the stent-graft by moving the stent-graft along its axis with reference to the first set of markers and rotating the stent-graft about its axis with reference to the set of markers.

40. The method of claim 38, wherein deploying the lower part of the stent-graft includes deploying a first section of the lower part having a long leg and a short leg and thereafter deploying a second section of the lower part by mating the second section with the short leg of the first section.

41. The method of claim 38, wherein deploying the lower part of the stent-graft includes using a sheath to advance the lower part of the stent-graft into a stem of the upper part of the stent-graft, withdrawing the sheath from the lower part of the stent-graft and expanding the lower part of the stent-graft.

42. The method of claim 38, wherein the upper part of the stent-graft is deployed so that the renal aperture and adjacent parts of the graft material and stent system, located above a bottom of the renal aperture, lie above the proximal portion of the aneurysm.

43. A stent-graft system for bridging an aneurysm in an aorta, the aneurysm being at least partially disposed between two renal arteries and two iliac arteries, comprising: a stent-graft including;
a graft material defining at least one renal aperture oriented to align with one of the two renal arteries when the stent-graft is in an expanded state; and
a stent system for supporting the graft material in a contracted state wherein each renal aperture is contracted and the expanded state wherein each renal aperture is expanded;
wherein each renal aperture is larger than the orifice of the respective renal artery.
wherein the stent-graft includes an upper section including an upper part of the stent system and an upper part of the graft material, the upper section including the renal aperture and being adapted to extend from above the aneurysm to a region within the aneurysm; and
wherein the stent-graft includes a lower section including a lower part of the stent system and a lower part of the graft material, the lower section being adapted to extend from the upper section of graft material beyond the aneurysm; and
a delivery system operable with the upper section of the stent-graft to partially expand the upper section independent of the lower section and to position and rotate the upper section of the stent-graft while partially expanded for aligning the renal aperture with its respective artery.

44. The stent-graft system of claim 43, wherein the at least one renal aperture defines the opening sufficiently larger than the orifice of the respective renal artery so that a perimeter of the opening presses against a wall of the aorta.

45. The stent-graft system of claim 43, wherein the delivery system includes a balloon for expanding the upper section of the stent-graft.

46. The stent-graft system of claim 43, wherein the lower section includes a longer leg and a shorter leg and wherein the stent-graft includes a mating leg, the longer leg of the lower section being adapted to extend into a first one of the iliac arteries and the mating leg being adapted to extend from the shorter leg of the lower section into a second one of the iliac arteries.

\* \* \* \* \*